(12) United States Patent
Sugimura et al.

(10) Patent No.: US 9,086,395 B2
(45) Date of Patent: Jul. 21, 2015

(54) AUTOMATIC ANALYSIS APPARATUS

(75) Inventors: Tomohiro Sugimura, Otawara (JP);
Shoichi Kanayama, Otawara (JP)

(73) Assignees: KABUSHIKI KAISHA TOSHIBA,
Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/116,697

(22) Filed: May 26, 2011

(65) Prior Publication Data

US 2011/0293474 A1 Dec. 1, 2011

(30) Foreign Application Priority Data

May 28, 2010 (JP) .................. 2010-123219

(51) Int. Cl.
*G01N 35/10* (2006.01)
(52) U.S. Cl.
CPC .................. *G01N 35/1004* (2013.01)
(58) Field of Classification Search
CPC .................. G01N 35/1004
See application file for complete search history.

(56) References Cited

U.S. PATENT DOCUMENTS

2002/0134117 A1 * 9/2002 Arai et al. ............... 68/3 SS

FOREIGN PATENT DOCUMENTS

| JP | 63-262568 | | 10/1988 |
|----|-----------|---|---------|
| JP | 2950698 | | 7/1999 |
| JP | 2001305148 | * | 10/2001 |
| JP | 2002-62303 | | 2/2002 |
| JP | 2005-241442 | | 9/2005 |
| JP | 2006-126016 | * | 5/2006 |
| JP | 2008-224244 | | 9/2008 |
| JP | 2008-224245 | | 9/2008 |
| WO | WO 2008108328 | * | 9/2008 |

* cited by examiner

*Primary Examiner* — P. Kathryn Wright
(74) *Attorney, Agent, or Firm* — Oblon, McClelland, Maier & Neustadt, L.L.P.

(57) ABSTRACT

In one embodiment, an automatic analysis apparatus includes a nozzle, first and second modifying units, a supply unit and a control unit. The control unit respectively controls the first and second modifying units and the supply unit to perform a first step of producing a first flow path state, a second step of producing a second orifice state and a second flow path state, a third step of producing the first flow path state, and a fourth step of producing a first orifice state. The first flow path state causing a fluid to be discharged from the flow path. The second flow path state causing the fluid to be sucked into the flow path. The first orifice state causing the orifice to be located in the air. The second orifice state causing the orifice to be located in a detergent.

6 Claims, 11 Drawing Sheets

AUTOMATIC ANALYSIS APPARATUS

CROSS-REFERENCE TO RELATED APPLICATIONS

This application is based upon and claims the benefit of priority from Japanese Patent Application No. 2010-123219, filed May 28, 2010; the entire contents of which are incorporated herein by reference.

FIELD

Embodiments described herein relate generally to an automatic analysis apparatus.

BACKGROUND

An automatic analysis apparatus is intended for, for example, biochemical or immunological inspection items, and analyzes a sample (test sample) such as blood. Specifically, the automatic analysis apparatus measures, as a change in translucent characteristic, a change in tone or turbidity caused by a chemical reaction to a mixture of the sample and a reagent corresponding to each inspection item. Thereby, the automatic analysis apparatus measures the density of various components in the sample and the activity of enzymes.

This automatic analysis apparatus measures one or more inspection items selected in accordance with the object of an inspection from a great number of inspection items that are measurable in a set analytical condition. The test sample is then dispensed by a sample probe from a sample container stored in a sample probe sampler to a reaction container. The reagent is dispensed by a reagent probe from a reagent container stored in a reagent probe reagent storage to the reaction container. The test sample and the sample dispensed to the reaction container are then stirred by a stirrer. Further, the translucent characteristic of the mixture of the sample and the reagent in the reaction container is measured by a photometry unit. The sample probe and the reagent probe are washed whenever the dispensation of the test sample and the reagent is finished. If this washing is insufficient, test samples and reagents used in past inspections are mixed in a reaction solution for a new inspection. This is called a carryover, and causes a decrease in the accuracy of a new inspection.

Accordingly, various techniques for washing the sample probe have been proposed.

For example, Japanese Patent No. 2950698 has disclosed that a detergent for washing the sample probe is contained in a reagent container for containing reagents, and the detergent is sucked by the sample probe and discharged to a washing basin to carry out washing with the detergent.

However, according to the above-mentioned technique, a long time has to be taken for horizontal movement of the sample probe during the process of washing the sample probe. Therefore, there has been a problem of the increased time taken from the start of the washing process to the end.

Under such circumstances, there has been a desire to reduce a cycle time by minimizing the time taken for the movement of a nozzle such as the sample probe in washing this nozzle.

DETAILED DESCRIPTION

In general, according to one embodiment, an automatic analysis apparatus includes a nozzle, a first modifying unit, a second modifying unit, a washing water supply unit and a control unit. The nozzle includes a flow path, and an orifice that opens the flow path to the outside. The first modifying unit modifies the state of the flow path to selectively produce flow path states including at least a first flow path state and a second flow path state, the first flow path state causing a fluid to be discharged from the flow path, the second flow path state causing the fluid to be sucked into the flow path. The second modifying unit modifies the state of the orifice to selectively produce orifice states including at least a first orifice state and a second orifice state, the first orifice state causing the orifice to be located in the air, the second orifice state causing the orifice to be located in a detergent. The washing water supply unit supplies washing water to an outer wall of the nozzle. The control unit respectively controls the first modifying unit, the second modifying unit, and the washing water supply unit to perform a first step of producing the first flow path state to discharge the liquid matter in the flow path and inner water in the flow path, a second step of producing the second orifice state and the second flow path state after the first step to suck the detergent into the flow path, a third step of producing the first flow path state after the second step to discharge the detergent sucked into the flow path and the inner water, and a fourth step of producing the first orifice state after or in parallel with the third step and supplying the washing water to wash the outer wall of the nozzle.

Hereinafter, embodiments will be described with reference to the drawings.

First Embodiment

Figure 1:
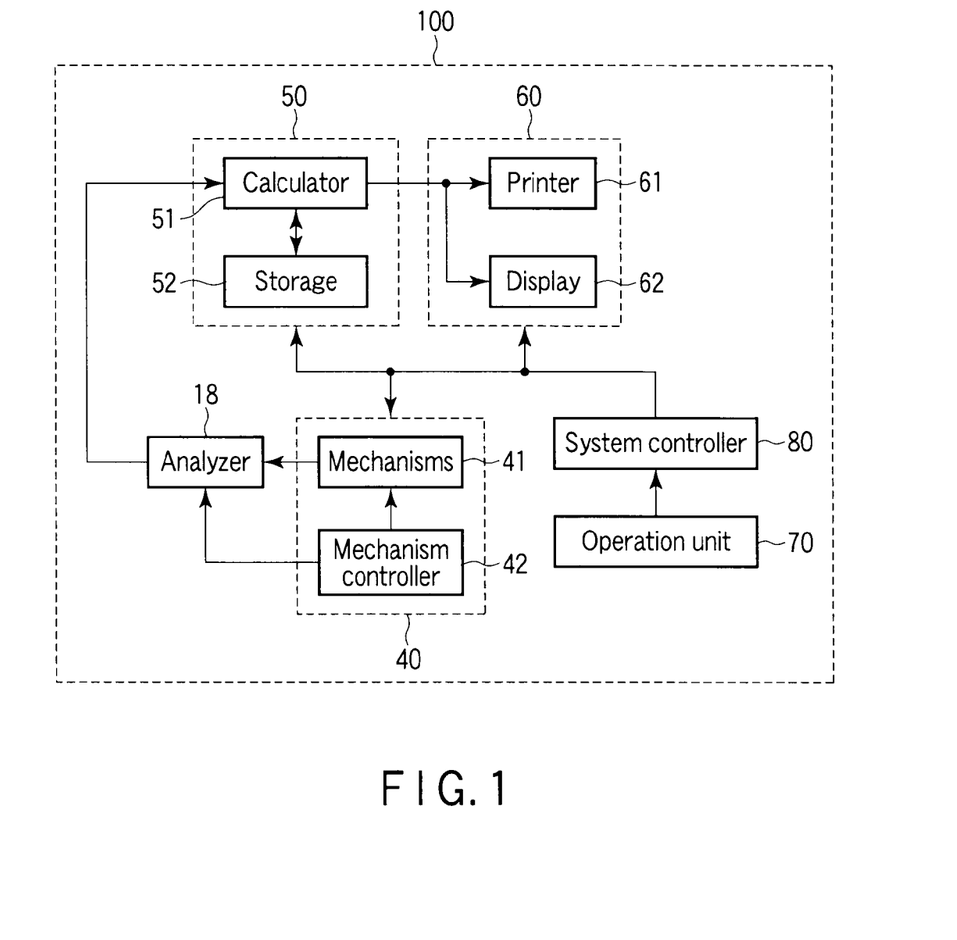
FIG. 1 is a block diagram showing the configuration of an automatic analysis apparatus according to an example.

FIG. 1 is a block diagram showing the configuration of an automatic analysis apparatus 100 according to a first embodiment.

This automatic analysis apparatus 100 comprises an analyzer 18, a driver 40, a data processor 50, an output unit 60, and operation unit 70, and a system controller 80.

The analyzer 18 measures the translucent characteristic of a mixture of a sample such as a test sample or a reference sample corresponding to various inspection items, and a reagent corresponding to various inspection items. The analyzer 18 outputs reference sample data indicating measurement results of the reference sample, and test sample data indicating measurement results of the test sample.

The driver 40 drives units included in the analyzer 18. More specifically, the driver 40 includes mechanisms 41 and a mechanism controller 42. The mechanisms 41 include mechanisms for driving the above-mentioned units, respectively. The mechanism controller 42 controls the operations of the mechanisms included in the mechanisms 41 and thereby controls the operations of the above-mentioned units.

The data processor 50 processes the reference sample data and the test sample data to create analytical curves and generate analytical data. More specifically, the data processor 50 includes a calculator 51 and a storage 52. The calculator 51 creates the analytical curves from the reference sample data and the test sample data. The storage 52 comprises, for example, a hard disk, and saves the analytical curve for each inspection item. The calculator 51 also reads, from the storage 52, the analytical curve of the inspection item corresponding to photometry unit test sample data. Using the read analytical curve, the calculator 51 then generates the analytical data on, for example, the density and activity values of components corresponding to the inspection item from the test sample data. The storage 52 saves the analytical data for each inspection item for each test sample. The analytical curve and the analytical data are output to the output unit 60.

The output unit 60 outputs the analytical curve and the analytical data. More specifically, the output unit 60 includes a printer 61 and a display 62. In accordance with a preset format, the printer 61 prints the analytical curve and the analytical data output from the data processor 50 on printing paper. The display 62 comprises a display device such as a CRT or a liquid crystal panel, and displays a screen that shows the analytical curve and the analytical data output from the data processor 50. The display 62 also displays various setting screens and selection screens. One of the setting screens is a screen for setting an analytical condition for, for example, the amount of a sample for each inspection item, the amounts of various reagents, or a wavelength. One of the setting screens is a screen for setting information (subject information) on a subject, for example, the ID or name of the subject. One of the setting screens is a screen for selecting an inspection item to be measured for each test sample.

The operation unit 70 comprises input devices such as a keyboard, a mouse, buttons, and a touch key panel. The operation unit 70 receives operations performed by an operator to specify various commands, the analytical condition for each inspection item, the subject information, or an inspection item to be measured for each test sample.

The system controller 80 comprises a central processing unit (CPU) and a memory. The CPU judges a command signal, the analytical condition, the subject information, or the inspection item specified in accordance with the operation performed in the operation unit 70. The memory stores the information judged by the CPU. The CPU performs overall control of the driver 40, the data processor 50, and the output unit 60 on the basis of the information stored in the memory.

Figure 2:
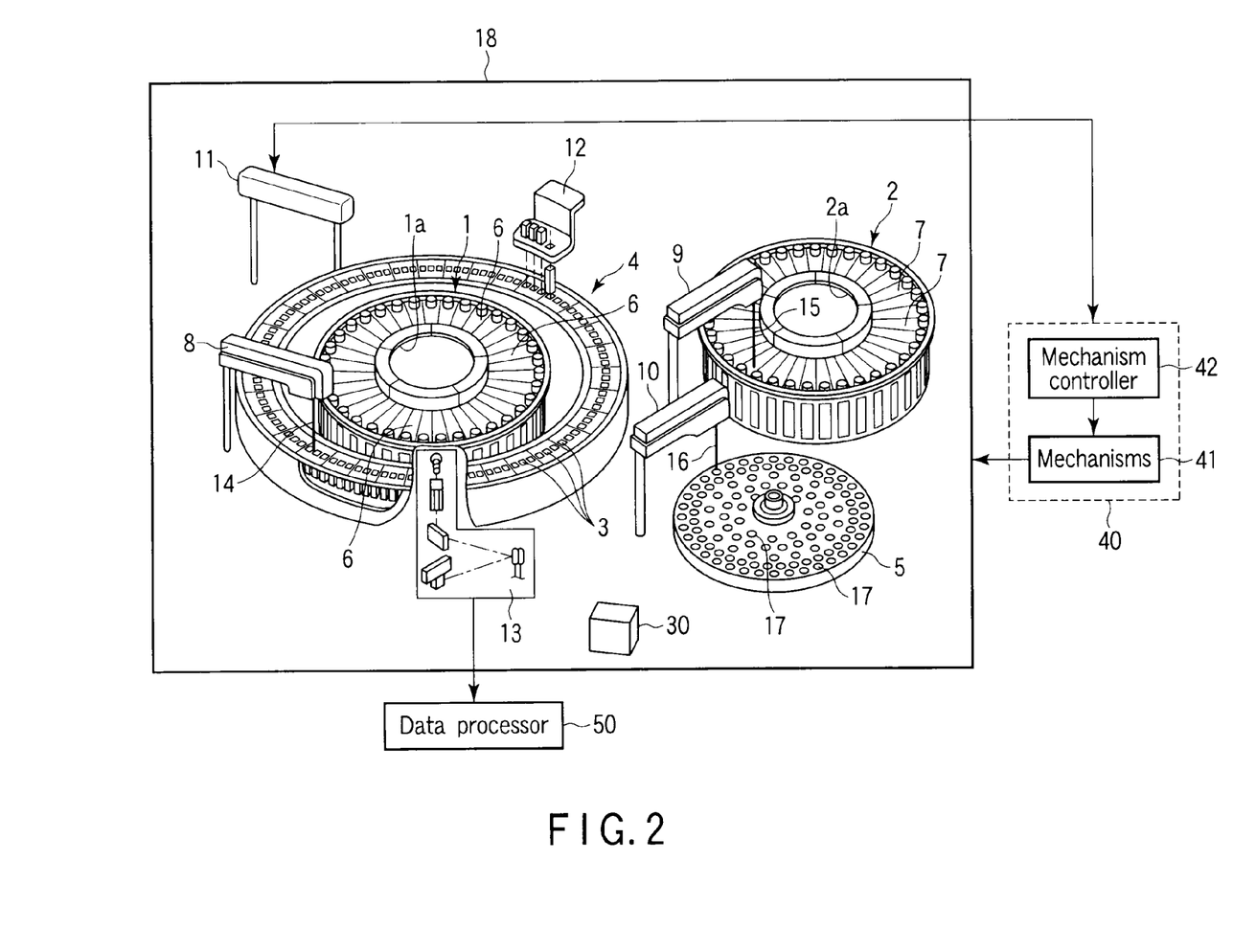
FIG. 2 is a perspective view showing the structure of an analyzer in FIG. 1.

FIG. 2 is a perspective view showing the structure of the analyzer 18.

The analyzer 18 comprises a first reagent storage 1, a second reagent storage 2, reaction containers 3, a reaction disk 4, a disk sampler 5, reagent containers 6, reagent containers 7, a first reagent arm 8, a second reagent arm 9, a sample arm 10, a stirring unit 11, a washing unit 12, a photometry unit 13, a first reagent probe 14, a second reagent probe 15, a sample probe 16, sample containers 17, and a washing unit 30.

The first reagent storage 1 stores a rack 1a that rotatably holds the reagent container 6.

The second reagent storage 2 stores a rack 2a that rotatably holds the reagent container 7.

The reaction container 3 contains a first mixture of a sample and a first reagent, and a second mixture of the sample, the first reagent, and a second reagent.

The reaction disk 4 holds, rotatably movably along a circumference, multiple reaction containers 3 arranged at regular intervals on the circumference.

The disk sampler 5 is rotatable, holds, around its rotation axis, a great number of sample containers 17.

The reagent container 6 contains the first reagent that reacts with the component for each inspection item contained in the sample.

The reagent container 7 contains the second reagent that pairs with the first reagent.

The first reagent arm 8 rotatably and vertically movably holds the first reagent probe 14.

The second reagent arm 9 rotatably and vertically movably holds the second reagent probe 15.

The sample arm 10 rotatably and vertically movably holds the sample probe 16.

The stirring unit 11 stirs the first mixture or the second mixture contained in the reaction container 3.

The washing unit 12 includes a washing nozzle, a drying nozzle, and a holding member. The washing nozzle sucks the first mixture or the second mixture in the reaction container 3, and also discharges a washing solution for washing the inside of the reaction container 3. The drying nozzle dries the inside of the reaction container 3. The holding member vertically movably holds the washing nozzle and the drying nozzle.

The photometry unit 13 applies light to the reaction container 3 located at a photometric position, and measures the translucent characteristic of the mixture contained in the reaction container 3. The translucent characteristic measured by the photometry unit 13 is generally an absorbance. The photometry unit 13 then generates the reference sample data from the absorbance measured when the mixture including the reference sample is contained in the reaction container 3 located at the photometric position. The photometry unit 13 also generates the test sample data from the absorbance measured when the mixture including the test sample is contained in the reaction container 3 located at the photometric position. Further, the photometry unit 13 outputs the reference sample data or the test sample data to the data processor 50.

The first reagent probe 14 dispenses the first reagent in each dispensing cycle. It should be understood that dispensing the first reagent means discharging the first reagent sucked from the reagent container 6 into the reaction container 3.

The second reagent probe 15 dispenses the second reagent in each dispensing cycle. It should be understood that dispensing the second reagent means discharging the second reagent sucked from the reagent container 7 into the reaction container 3.

The sample probe 16 dispenses the sample in each dispensing cycle. It should be understood that dispensing the sample means discharging the sample sucked from the sample container 17 into the reaction container 3.

The sample container 17 contains samples.

The washing unit 30 washes the sample probe 16.

The mechanisms 41 comprise the following mechanisms: a mechanism for turning the rack 1a; a mechanism for turning the rack 2a; a mechanism for turning the disk sampler 5; a mechanism for turning the reaction disk 4; a mechanism for rotating and vertically moving the sample arm 10; a mechanism for rotating and vertically moving the first reagent arm 8; a mechanism for rotating and vertically moving the second reagent arm 9 and a mechanism for rotating and vertically moving part of the stirring unit 11; or a mechanism for vertically moving the washing unit 12. The mechanisms included in the mechanisms 41 comprise the following various pumps: a dispensing pump for causing the sample probe 16 to suck and discharge the sample; first and second reagent pumps for causing the first and second reagent probes 14 and 15 to suck and discharge the first and second reagents; a washing pump for sucking the first mixture or the second mixture from the washing nozzle of the washing unit 12 and for discharging and sucking the washing solution; and a drying pump for sucking from the drying nozzle of the washing unit 12.

Figure 3:
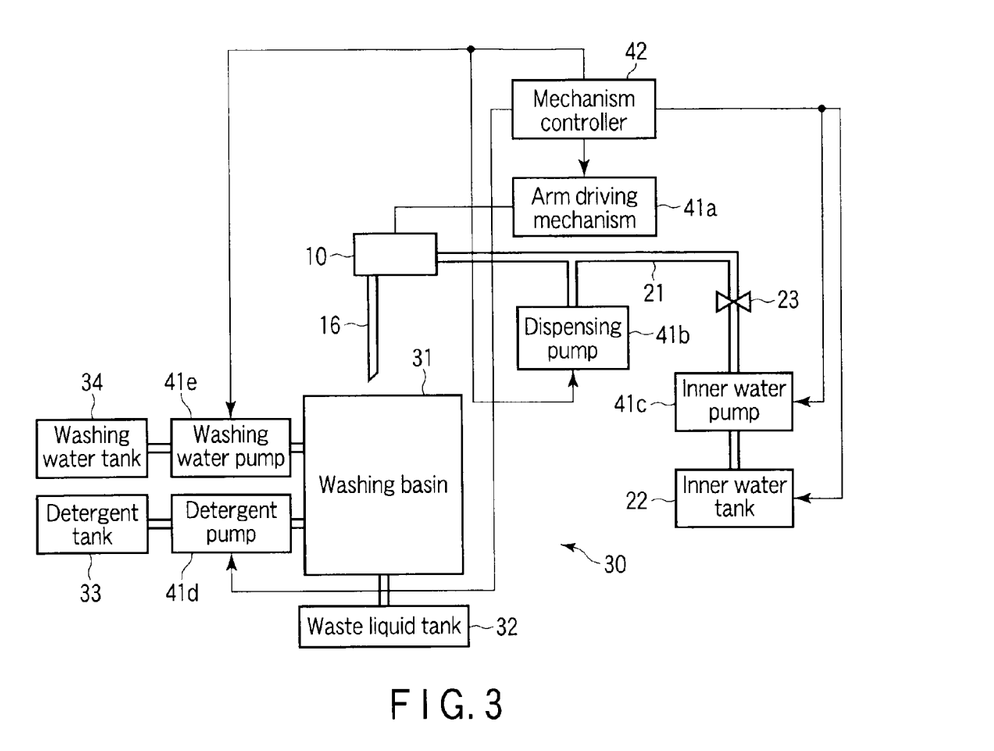
FIG. 3 is a diagram showing the configuration of a washing unit.

FIG. 3 is a diagram showing the configuration of the washing unit 30. FIG. 3 also shows the sample arm 10, the sample probe 16, the mechanism controller 42, and some of the mechanisms 41. Some of the mechanisms 41 shown in FIG. 3 are an arm driving mechanism 41a, a dispensing pump 41b, an inner water pump 41c, a detergent pump 41d, and a washing water pump 41e. All of these pumps are controlled by the mechanism controller 42.

The sample probe 16 changes in its horizontal position when the sample arm 10 is rotated by the arm driving mechanism 41a. The sample probe 16 changes in its vertical position when the sample arm 10 is vertically moved by the arm driving mechanism 41a.

The sample probe 16 is in the shape of a nozzle having therein a space (hereinafter referred to as an internal flow path) serving as a flow path of a liquid matter such as a sample. The dispensing pump 41b and the inner water pump 41c are connected to the sample probe 16 via a tube 21 which is connected to be in communication with the internal flow path.

The dispensing pump 41b sucks inner water filling the tube 21 to cause negative pressure in the internal flow path and suck the sample into the internal flow path. The dispensing pump 41b also comprises a fluid discharge device that discharges the inner water into the tube 21 to discharge the sample from the internal flow path.

The inner water pump 41c discharges the inner water retained in an inner water tank 22 into the tube 21 to discharge the inner water from the sample probe 16.

The inner water pump 41c has such a high discharge volume that enables the inner water to be discharged from the sample probe 16 at a certain pace. In contrast, the dispensing pump 41b is lower in discharge volume than the inner water pump 41c, but is capable of highly precisely adjusting the amount of sucking the sample into the sample probe 16 and the amount of discharging the sample from the sample probe 16.

Now, the washing unit 30 includes a washing basin 31, a waste liquid tank 32, a detergent tank 33, and a washing water tank 34.

The washing basin 31 has therein a space open in its upper part. In this space, the sample probe 16 is washed.

The waste liquid tank 32 contains a liquid which has flowed out of the washing basin 31.

The detergent tank 33 retains a detergent (liquid detergent) for washing the sample probe 16. The detergent retained by the detergent tank 33 is, for example, an alkaline detergent. The detergent retained by the detergent tank 33 is supplied to the washing basin 31 by the detergent pump 41d.

The washing water tank 34 retains washing water for washing the sample probe 16. The washing water retained by the washing water tank 34 is supplied to the washing basin 31 includes a main body 311 and a partition (protrusion) 312.

Figure 4:
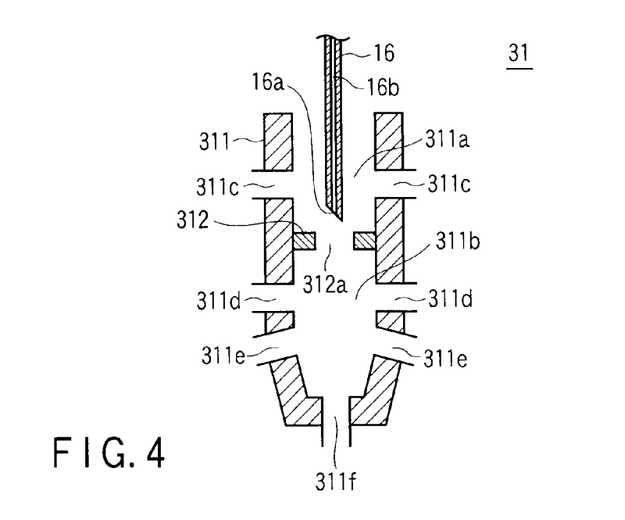
FIG. 4 is a sectional view showing the structure of a washing basin in FIG. 3 according to a first embodiment.

FIG. 4 is a sectional view showing the structure of the washing basin 31. FIG. 4 also shows the section of the distal end of the sample probe 16.

A reference number 16b in FIG. 4 denotes the above-mentioned internal flow path. This internal flow path 16b is open to the outside at the distal end of the sample probe 16. Thus, an orifice 16a is formed at the distal end of the sample probe 16.

The washing basin 31 includes a main body 311 and a partition 312.

The main body 311 has an elongate internal space along the vertical direction. This internal space is open in its upper part, and is not capable of preventing the entry of the sample probe 16.

The partition 312 is made of a plate-like material. The partition 312 is located in the vicinity of the center of the internal space of the main body 311 in a substantially horizontal posture, and is fixed to the main body 311. The partition 312 has an opening 312a in the center. The diameter of the opening 312a is larger than the outside diameter of the sample probe 16. Thus, the partition 312 has a protrusion formed to protrude into the internal space of the main body 311 so that the movement of the sample probe 16 in the vertical direction may not be prevented. The partition 312 may be formed integrally with the main body 311.

The internal space of the main body 311 is divided into two spaces arranged in the vertical direction across the partition 312. Hereinafter, the upper one of the two spaces is referred to as an upper space or washing container 311a, and the lower one is referred to as a lower space or retention container 311b.

Water supply holes 311c, detergent supply holes 311d, upper waste liquid holes 311e, and a lower waste liquid hole 311f are formed in the main body 311.

The water supply holes 311c are formed through the sidewall of the main body 311 from the upper space 311a to the outside of the main body 311. The washing water pump 41e is connected to the water supply holes 311c via, for example, a tube, whereby the washing water tank 34, the washing water pump 41e and the water supply holes 311c comprise a supplying unit for supplying washing water to the washing container.

The detergent supply holes 311d are formed through the sidewall of the main body 311 from the lower space 311b to the outside of the main body 311. The detergent pump 41d is connected to the detergent supply holes 311d via, for example, a tube.

The upper waste liquid holes 311e are formed through the sidewall of the main body 311 from the lower space 311b to the outside of the main body 311. The upper waste liquid holes 311e are connected to the waste liquid tank 32 via, for example, a tube.

The lower waste liquid hole 311f is formed through the lower wall of the main body 311 from the lower space 311b to the outside of the main body 311. The lower waste liquid hole 311f is connected to the waste liquid tank 32 via, for example, a tube. The lower waste liquid hole 311f is desirably aligned with the opening 312a along the vertical direction.

The operation of the automatic analysis apparatus 100 is described next. However, most of the operation for analyzing components contained in a liquid matter such as blood or urine may be similar to the operation of other existing automatic analysis apparatuses and is therefore not described here. The operation associated with the washing of the sample probe 16 is described in detail here.

When the dispensation of a sample to the reaction container 3 is finished, the sample probe 16 is washed under the control of the mechanism controller 42 as follows.

Figure 5:
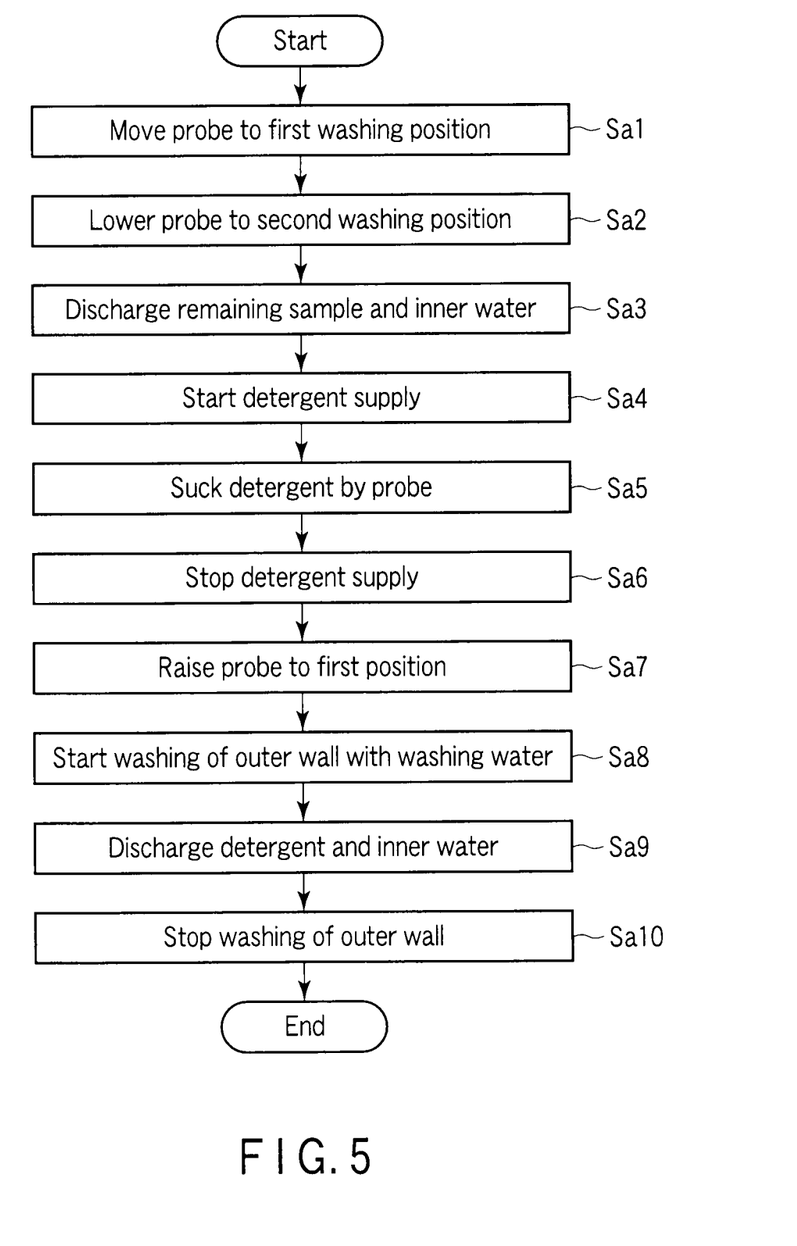
FIG. 5 is a flowchart showing a processing procedure of a mechanism controller according to the first embodiment.

FIG. 5 is a flowchart showing a processing procedure of the mechanism controller 42 for washing the sample probe 16.

In step Sa1, the mechanism controller 42 moves the sample probe 16 to a first washing position. The first washing position is a position shown in FIG. 4. That is, when the sample probe 16 is at the first washing position, the distal end of the sample probe 16 is located in the upper space 311a, and the whole sample probe 16 is located above the opening 312a. Therefore, more specifically, the mechanism controller 42 raises the sample arm 10 to pull the sample arm 10 from the reaction container 3, and rotates the sample arm 10 to move the sample probe 16 to the position above the opening 312a.

Figure 6:
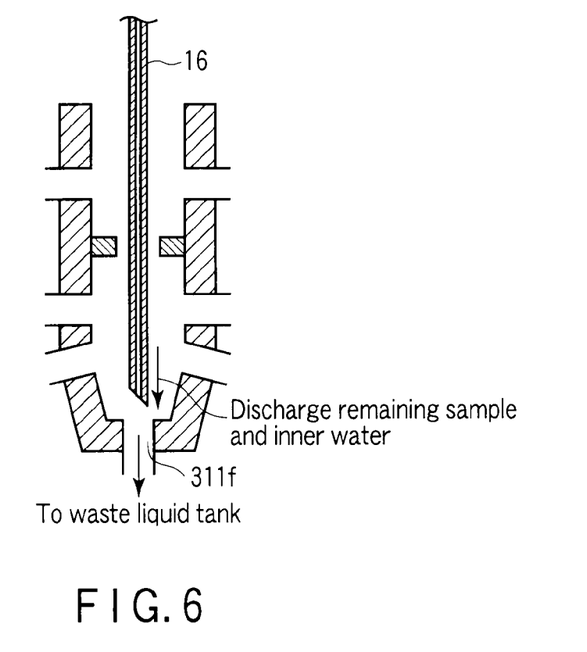
FIG. 6 is a diagram showing a condition in which a sample probe is located at a second washing position.

In step Sa2, the mechanism controller 42 lowers the sample arm 10 to lower the sample probe 16 to a second washing position shown in FIG. 6.

In step Sa3, the mechanism controller 42 causes the sample (remaining sample) remaining in the internal flow path 16b of the sample probe 16 and the inner water to be discharged from the sample probe 16 as shown in FIG. 6. More specifically, the mechanism controller 42 causes the inner water retained in the inner water tank 22 to be discharged from the inner water pump 41c, and thereby causes the remaining sample to be discharged from the sample probe 16. The mechanism controller 42 then actuates the inner water pump 41c until the discharge of the remaining sample is finished and the inner water is discharged from the sample probe 16. The amount of the remaining sample is known. Therefore, the time for continuing the operation of the inner water pump 41c here can be determined in advance in consideration of the amount of the remaining sample and the discharge volume of the inner water pump 41c.

In this way, the inner wall of the sample probe 16 is washed with the inner water after the remaining sample is discharged.

Here, the mechanism controller 42 could control the dispensing pump 41b to discharge the remaining sample in the internal flow path 16b of the sample probe 16 and the inner water from the sample probe 16 instead of the inner water pump 41c.

The remaining sample discharged from the sample probe 16 and the inner water flow out of the lower waste liquid hole 311f and are collected in the waste liquid tank 32. In this case, as long as the lower waste liquid hole 311f is aligned with the opening 312a along the vertical direction, the sample probe 16 can insert the orifice 16a into the lower waste liquid hole 311f. If the remaining sample and the inner water are discharged in such a condition, most of the remaining sample discharged from the sample probe 16 directly passes through the lower waste liquid hole 311f. As a result, the amount of the remaining sample adhering to the inner wall of the washing basin 31 due to the scattering of the remaining sample can be reduced.

Figure 7:
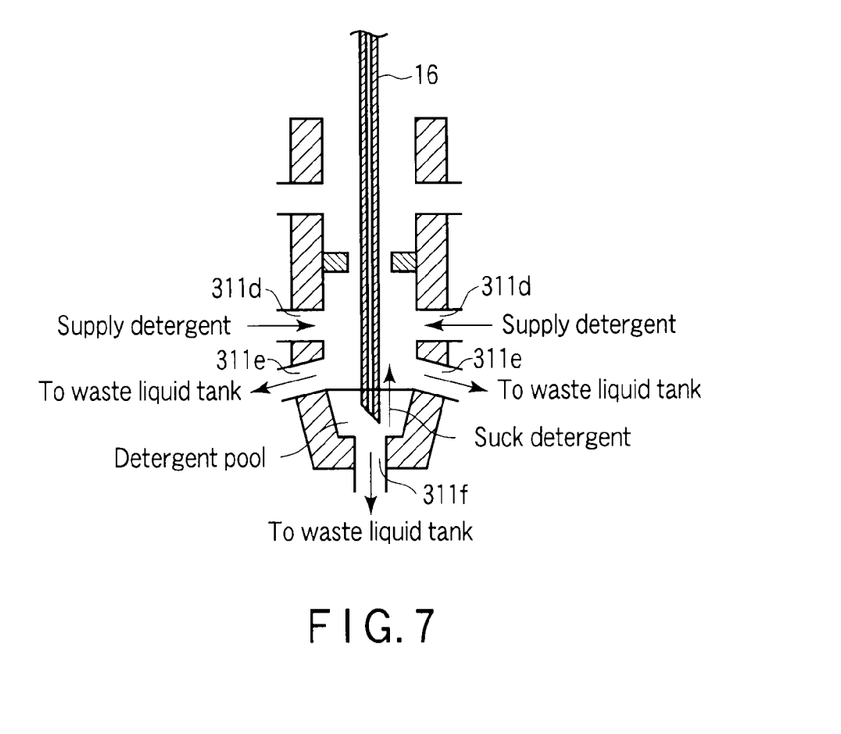
FIG. 7 is a diagram showing a condition in which a detergent pool is formed.

In step Sa4, the mechanism controller 42 starts the operation of the detergent pump 41d, and starts the supply of the detergent to the washing basin 31. Thus, the detergent sent from the detergent tank 33 by the detergent pump 41d flows into the lower space 311b from the detergent supply holes 311d. The detergent which has flowed into the lower space 311b flows out of the lower waste liquid hole 311f by its weight at a given velocity. The discharge amount of the detergent pump 41d is set so that the velocity of supplying the detergent to the lower space 311b may be higher than the velocity of the detergent flowing out of the lower waste liquid hole 311f. Thus, a detergent pool is formed in the lower part of the lower space 311b as shown in FIG. 7. When the fluid level of the detergent pool surpasses the condition shown in FIG. 7, the detergent flows out of the upper waste liquid holes 311e. Thus, the detergent pool is maintained in the condition shown in FIG. 7, and the fluid level of the detergent pool is adjusted to a constant level. The second washing position is determined to provide the condition shown in FIG. 7 in which the distal end of the sample probe 16 in brought into the detergent pool.

In step Sa5, the mechanism controller 42 causes the sample probe 16 to suck the detergent. More specifically, the mechanism controller 42 causes the dispensing pump 41b to function as a fluid suction device and perform the suction operation in a given period to cause the sample probe 16 to suck a certain amount of detergent. Here, the amount of detergent sucked by the sample probe 16 may be changed in accordance with the kind and amount of remaining sample. More specifically, the amount of detergent to be sucked is increased in accordance with an increase in the viscosity of the remaining sample.

Alternatively, the amount of detergent to be sucked is increased in accordance with an increase in the quantity of the remaining sample. In this way, a higher washing efficiency can be expected.

Instead of changing the amount of detergent to be sucked, another kind of detergent may be used. The higher the alkalinity (also hereinafter referred to as "alkai") level of a detergent is, the more remarkable the washing effect becomes. Therefore, a detergent having a high alkali level is used when the viscosity of the remaining sample is high. Likewise, a detergent having a high alkali level is used when the amount of remaining sample is large. In general, the time between the start of the suction of a detergent and the completion of the discharge of the detergent is constant. Therefore, if the time required for the suction of the detergent is lengthened to increase the amount of detergent to be sucked, the time during which the detergent can stay inside the sample probe 16 is inevitably short. However, if a different kind of detergent is used without changing the amount of determined to be sucked, the time needed for the suction of the detergent does not have to be greatly changed. Accordingly, a more remarkable washing effect can be expected without shortening the time during which the detergent can stay inside the sample probe 16.

Moreover, in order to prevent the mixing of the detergent sucked here and the inner water, it is preferable to suck air in accordance with given timing before the discharge of the remaining sample and the inner water to form an air gap between the inner water and the detergent.

Here, the mechanism controller 42 could cause the inner water pump 41c to perform the suction operation in a given period to cause the sample probe 16 to suck a certain amount of detergent instead of the dispensing pump 41b.

The sample probe 16 sucks the detergent as described above, so that the inner wall of the sample probe 16 is washed with the detergent. At the same time, the outer wall of the sample probe 16 contacts the detergent during the above-mentioned suction of the detergent, and the outer wall of the sample probe 16 is thereby washed with the detergent.

When the suction of the detergent by the sample probe 16 is finished, the mechanism controller 42, in step Sa6, stops the operation of the detergent pump 41d, and stops the supply of the detergent to the washing basin 31. As a result, the detergent in the washing basin 31 flows out of the lower waste liquid hole 311f, and the detergent pool is eliminated.

Figure 8:
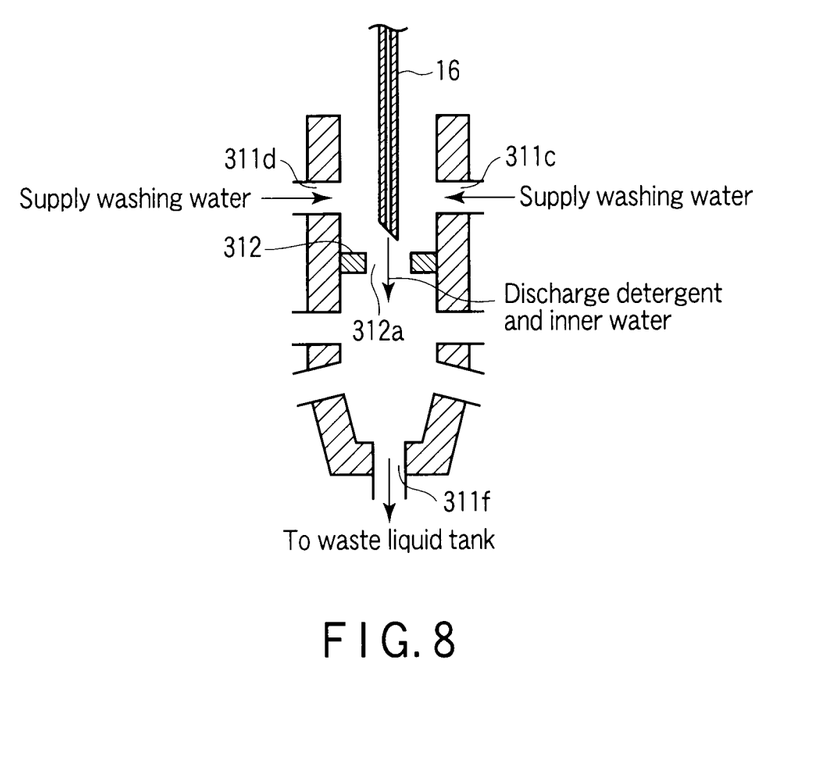
FIG. 8 is a diagram showing a condition in which the sample probe is located at a first washing position.

In step Sa7, the mechanism controller 42 raises the sample arm 10 to raise the sample probe 16 to the first washing position.

In step Sa8, the mechanism controller 42 starts the washing of the outer wall of the sample probe 16 with the detergent. More specifically, the mechanism controller 42 starts the operation of the washing water pump 41e, and supplies the washing water retained in the washing water tank 34 to the lower space 311b from the detergent supply holes 311d. Thus, as shown in FIG. 8, the outer wall of the sample probe 16 is washed with the washing water blowing from the detergent supply holes 311d. The washing water is collected into the waste liquid tank 32 via the opening 312a and the lower waste liquid hole 311f.

In step Sa9, the mechanism controller 42 causes the detergent and the inner water to be discharged from the sample probe 16 as shown in FIG. 8. More specifically, the mechanism controller 42 causes the inner water retained in the inner water tank 22 to be discharged from the inner water pump 41c, and thereby causes the detergent to be discharged from the sample probe 16. The mechanism controller 42 then operates the inner water pump 41c until the discharge of the detergent is finished and the inner water is discharged from the sample probe 16. The amount of the sucked detergent is known. Therefore, the time for continuing the operation of the inner water pump 41c here can be determined in advance in consideration of the amount of the detergent and the discharge volume of the inner water pump 41c.

In this way, the inner wall of the sample probe 16 is washed with the inner water after the detergent is discharged.

The detergent and the inner water discharged from the sample probe 16 are collected into the waste liquid tank 32 via the opening 312a and the lower waste liquid hole 311f.

In step Sa10, the mechanism controller 42 stops the operation of the washing water pump 41e to stop the washing of the outer wall of the sample probe 16.

As has been described above in step Sa4, step Sa5, and step Sa6, the supply of the detergent and the suction of the detergent by the sample probe 16 are carried out at the same time in the present embodiment. However, the mechanism controller 42 may otherwise control each of the units to bring the distal end of the sample probe 16 into the detergent retained in the main body 311 after stopping the supply of the detergent and suck the detergent. In this way, the sample probe 16 can be brought into the detergent retained in the main body 311 in a condition in which the supply of the detergent is stopped and the fluid level is stable. This ensures the detergent to contact the range of the outer wall of the sample probe 16 to be washed, and can prevent the detergent from unnecessarily adhering to parts out of this range.

Thus, the first embodiment allows the discharge of the remaining sample, the washing of the inner wall with the detergent, the washing of the inner wall with the washing water, the washing of the outer wall with the detergent, and the washing of the outer wall with the washing water, without horizontal movement of the sample probe 16. Therefore, the sample probe 16 can be efficiently washed in a short time.

Alternatively, a long time can be taken for keeping the detergent in the internal flow path 16b of the sample probe 16 within a limited time that can be used for one washing of the sample probe 16. This can further ensure the washing of the inner wall.

Furthermore, according to the first embodiment, the upper space 311a for washing the outer wall with the washing water and the lower space 311b for washing the inner wall with the detergent are separately formed side by side in the vertical direction, so that each of the washings can be performed in a separate space. Thus, the washing water after used to wash the outer wall of the sample probe 16, that is, the tainted washing water is discharged to the outside of the washing unit 30 by use of, for example, the partition 312, so that the amount of such washing water brought into the lower space 311b can be suppressed. As a result, the efficiency of washing can be improved.

Moreover, according to the first embodiment, the partition 312 is provided, so that the scattering of the remaining sample, the detergent, and the washing water can be prevented, and the efficiency of washing the outer wall with the washing water can be improved.

Second Embodiment

The general configuration of an automatic analysis apparatus 100 according to the second embodiment is similar to that according to the first embodiment, as shown in FIG. 1 to FIG. 3. The second embodiment is different from the first embodiment in the structure of the washing basin 31 and the procedure of washing the sample probe 16.

Figure 9:
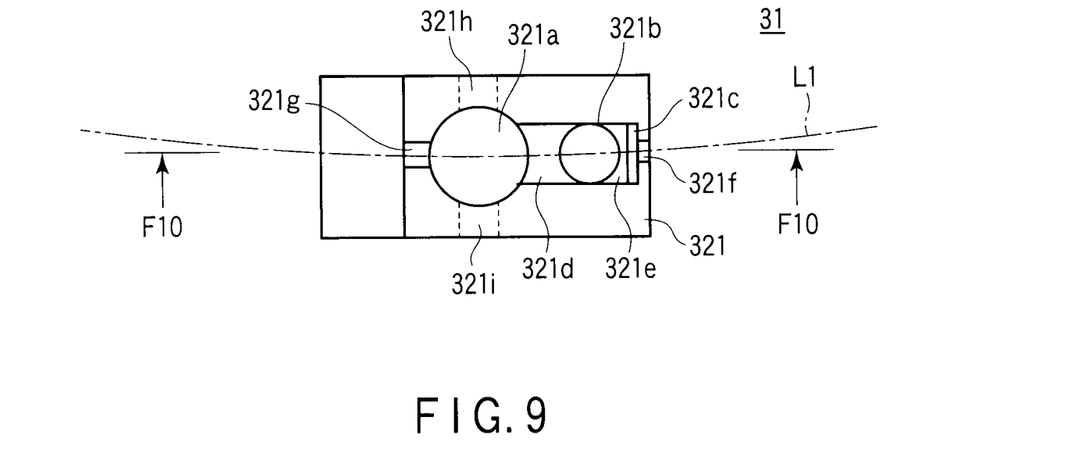
FIG. 9 is a plan view showing the structure of the washing basin in FIG. 3 according to a second embodiment.
Figure 10:
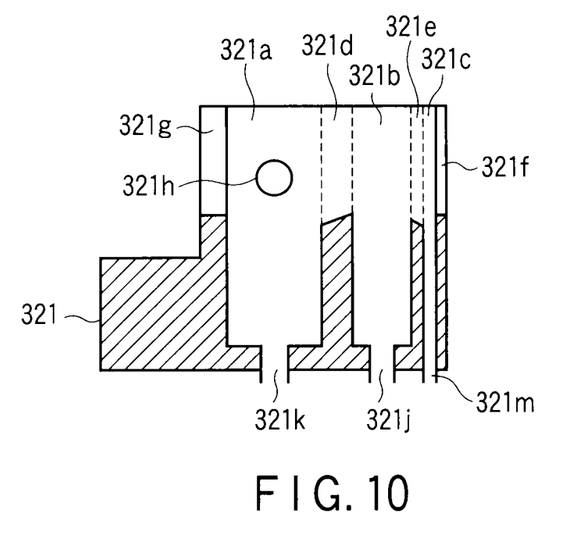
FIG. 10 is a sectional view along F10-F10 in FIG. 9.
Figure 11:
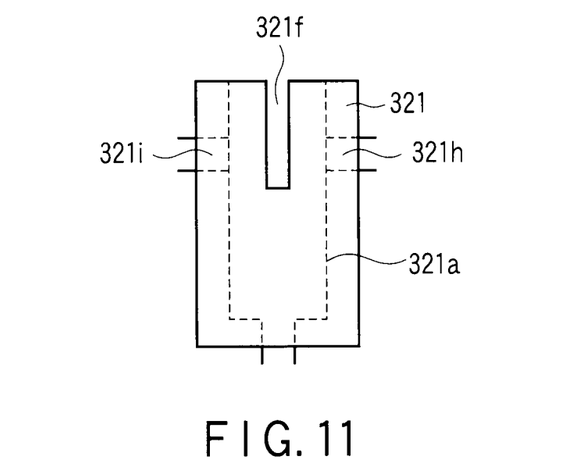
FIG. 11 is a plan view from the right side in FIG. 9.

FIG. 9 to FIG. 11 are diagrams showing the structure of the washing basin 31 according to the second embodiment. FIG. 9 is a plan view from above. FIG. 10 is a sectional view along F10-F10 in FIG. 9. FIG. 11 is a plan view from the right side in FIG. 9.

As shown in FIG. 9 to FIG. 11, the washing basin 31 according to the second embodiment includes a main body 321.

The main body 321 has an internal space along the vertical direction. This internal space is open in its upper part, and is not capable of preventing the entry of the sample probe 16.

The internal space of the main body 321 is divided into spaces 321a, 321b, 321c, 321d, and 321e.

The spaces 321a and 321b are both columnar, and parallel to each other. The generating line directions of the spaces 321a and 321b extend substantially along the vertical direction. The space 321c is in the shape of an elongate slit, and its longitudinal direction extends substantially along the vertical direction. The space 321a and the space 321c are located across the space 321b. The upper part of the space 321a and the upper part of the space 321c are connected via the space 321d. The upper part of the space 321b and the upper part of the space 321c are connected via the space 321e. The upper parts of all of these spaces 321a to 321e are open. The bottom surface of the space 321d is a slope that becomes lower from the space 321b toward the space 321a. The bottom surface of the space 321e is a slope that becomes lower from the space 321b toward the space 321c.

The main body 321 further has slits 321f and 321g. The slit 321f is in contact with the upper part of the space 321c, and is open to the outside of the main body 321 on the lateral side of the main body 321. The slit 321g is in contact with the upper part of the space 321a, and is open to the outside of the main body 321 on the lateral side of the main body 321.

The spaces 321a to 321e and the slits 321f and 321g are arranged substantially in line in the order of the slit 321f, the space 321c, the space 321e, the space 321b, the space 321d, the space 321a, and the slit 321g.

The main body 321 is disposed so that the spaces 321a to 321e and the slits 321f and 321g are arranged substantially along a movement track L1 of the sample probe 16 corresponding to the rotation of the sample arm 10, as shown in FIG. 9. The spaces 321a to 321e and the slits 321f and 321g are so sized as not to prevent the movement of the sample probe 16.

The main body 321 further has water supply holes 321h and 321i, a detergent supply hole 321j, and waste liquid holes 321k and 321m.

The water supply holes 321h and 321i are formed through different sidewalls of the main body 321 from the upper part of the space 321a to the outside of the main body 321. The washing water pump 41e is connected to the water supply holes 321h and 321i via, for example, a tube.

The detergent supply hole 321j is formed through the lower wall of the main body 321 from the space 321b to the outside of the main body 321. The detergent pump 41d is connected to the detergent supply hole 321j via, for example, a tube.

The waste liquid holes 321k and 321m are formed in the lower wall of the main body 321. The waste liquid hole 321k is formed to penetrate from the space 321a to the outside of the main body 321. The waste liquid hole 321m is formed to penetrate from the space 321c to the outside of the main body 321. The waste liquid holes 321k and 321m are connected to the waste liquid tank 32 via, for example, a tube. The waste liquid hole 321k is desirably aligned along the vertical direction with the intersection of the movement track L1 and a line that connects the water supply hole 321h and the water supply hole 321i.

The operation of the automatic analysis apparatus 100 according to the second embodiment is described next. However, most of the operation for analyzing components contained in a liquid matter such as blood or urine may be similar to the operation of other existing automatic analysis apparatuses and is therefore not described here. The operation associated with the washing of the sample probe 16 is described in detail here.

When the dispensation of a sample to the reaction container 3 is finished, the sample probe 16 is washed under the control of the mechanism controller 42 as follows.

Figure 12:
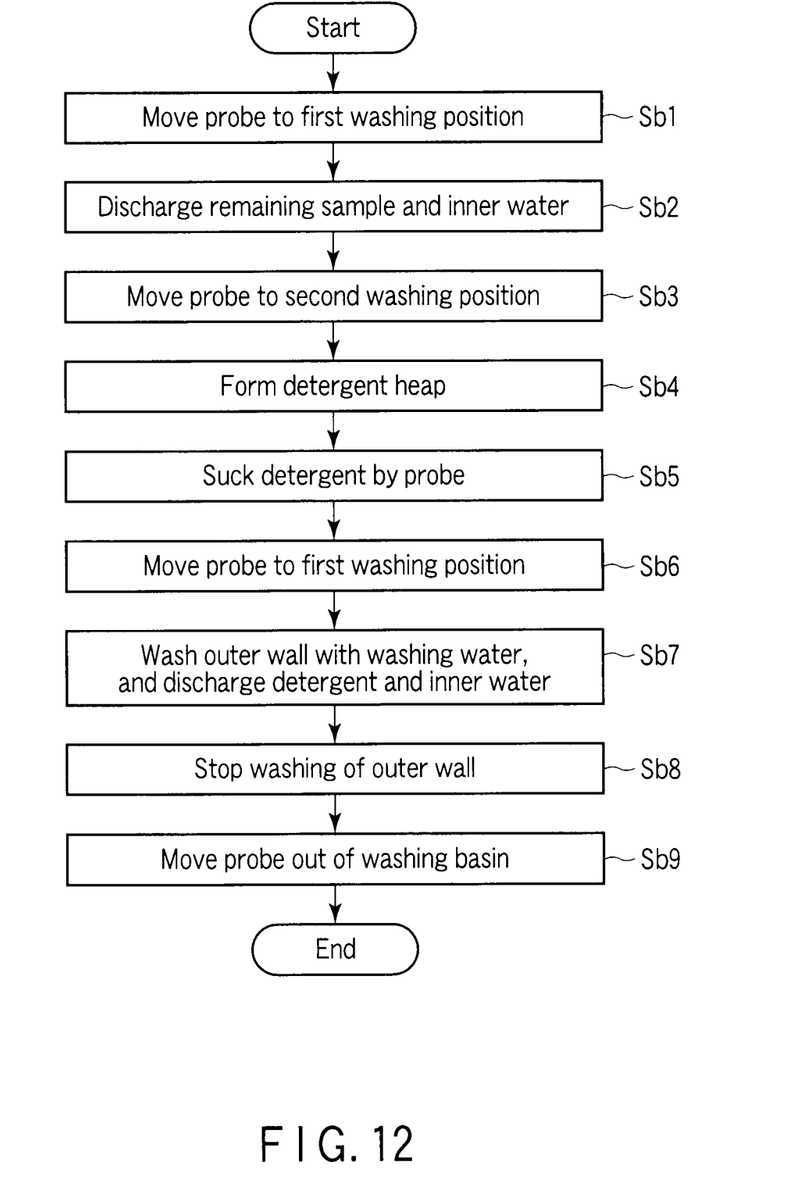
FIG. 12 is a flowchart showing a processing procedure of a mechanism controller according to the second embodiment.

FIG. 12 is a flowchart showing a processing procedure of the mechanism controller 42 for washing the sample probe 16.

Figure 13:
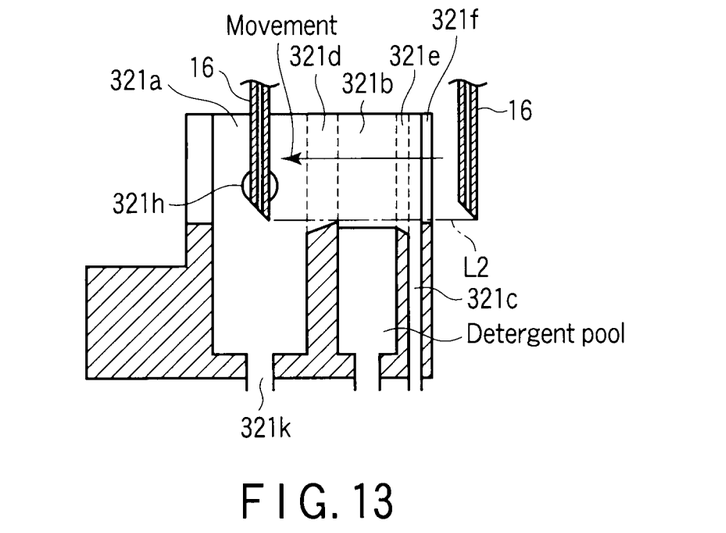
FIG. 13 is a diagram showing the step of moving the sample probe to a first washing position from the outside of the washing basin.

In step Sb1, the mechanism controller 42 moves the sample probe 16 from the outside of the washing basin 31 to a first washing position within the washing basin 31 as shown in FIG. 13. When the sample probe 16 is at the first washing position, the distal end of the sample probe 16 is located between the water supply hole 321h and the water supply hole 321i within the space 321a. Therefore, more specifically, the mechanism controller 42 raises the sample arm 10 to pull the sample arm 10 from the reaction container 3, and rotates the sample arm 10 to move the sample probe 16 to the space 321a through the slit 321f, the space 321c, the space 321e, the space 321b, and the space 321d. A chain line L2 in FIG. 13 indicates the movement track of the distal end of the sample probe 16 in this case.

In the meantime, a detergent pool produced from the detergent supplied by the detergent pump 41d from the detergent tank 33 via the detergent supply hole 321j is formed in the lower part of the space 321b, thereby forming a retention container, when step Sb1 is performed. The fluid level of the detergent pool is located lower than the movement track L2 by adjusting the amount of the detergent supplied by the detergent pump 41d. Therefore, the detergent does not contact the sample probe 16 that moves as described above.

Figure 14:
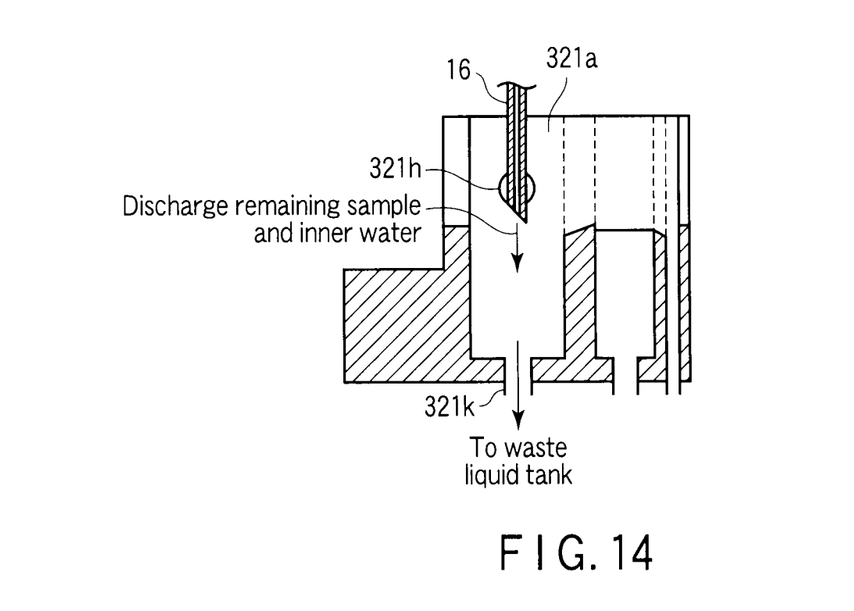
FIG. 14 is a diagram showing the step of discharging a remaining sample from the sample probe.

In step Sb2, the mechanism controller 42 causes the sample remaining in the internal flow path 16b of the sample probe 16 and the inner water to be discharged from the sample probe 16 as shown in FIG. 14. More specifically, the mechanism controller 42 causes the inner water retained in the inner water tank 22 to be discharged from the inner water pump 41c, and thereby causes the remaining sample to be discharged from the sample probe 16. The mechanism controller 42 then actuates the inner water pump 41c until the discharge of the remaining sample is finished and the inner water is discharged from the sample probe 16. The amount of the remaining sample is known. Therefore, the time for continuing the operation of the inner water pump 41c here can be determined in advance in consideration of the amount of the remaining sample and the discharge volume of the inner water pump 41c.

In this way, the inner wall of the sample probe 16 is washed with the inner water after the remaining sample is discharged.

The remaining sample and the inner water discharged from the sample probe 16 flow out of the waste liquid hole 321k and are collected in the waste liquid tank 32. In this case, if the waste liquid hole 321k is aligned along the vertical direction with the intersection of the movement track L1 and the line that connects the water supply hole 321h and the water supply hole 321i, the sample probe 16 at the first washing position is located substantially immediately above the waste liquid hole 321k. If the remaining sample and the inner water are discharged substantially exactly downward in such a condition, most of the remaining sample directly passes through the waste liquid hole 321k because the waste liquid hole 321k is located on the track of the remaining sample discharged from the sample probe 16. As a result, the scattering of the remaining sample in the bottom surface of the space 321a can be reduced.

Figure 15:
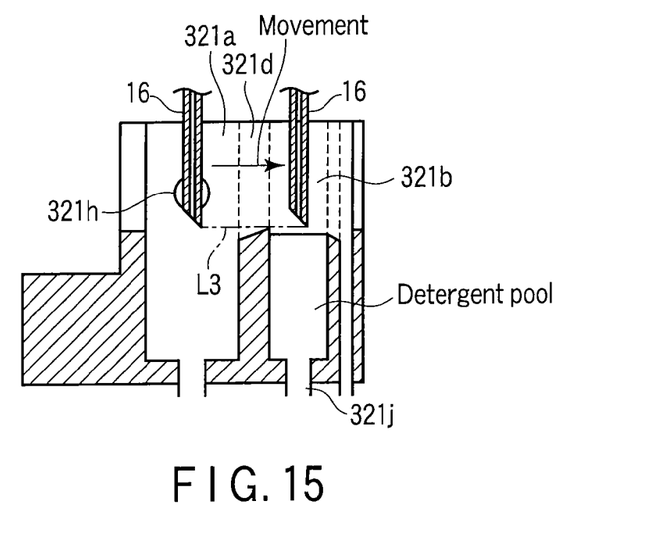
FIG. 15 is a diagram showing the step of moving the sample probe to a second washing position from the first washing position.

In step Sb3, the mechanism controller 42 moves the sample probe 16 from the first washing position to a second washing position as shown in FIG. 15. When the sample probe 16 is at the second washing position, the distal end of the sample probe 16 is located in the upper part of the space 321b. Therefore, more specifically, the mechanism controller 42 rotates the sample arm 10 to move the sample probe 16 to the space 321b through the space 321d. A chain line L3 in FIG. 15 indicates the movement track of the distal end of the sample probe 16 in this case. The movement track L3 corresponds to part of the movement track L2.

Figure 16:
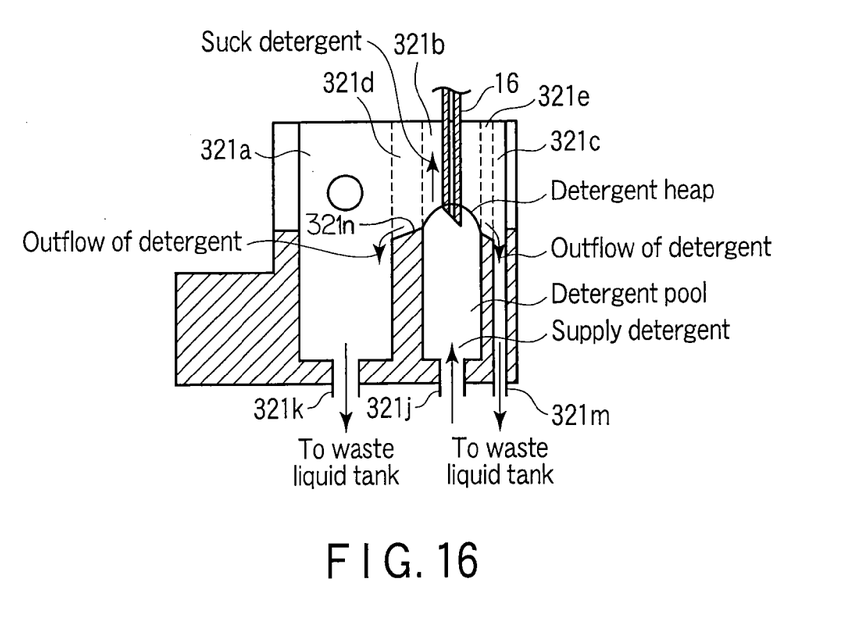
FIG. 16 is a diagram showing the step of washing the sample probe with a detergent.

In step Sb4, the mechanism controller 42 adjusts the supply amount of the detergent pump 41d to form a detergent heap as shown in FIG. 16. In this case, the orifice 16a is located within the detergent heap.

Moreover, extra detergent overflows the barrier 321n (see FIG. 16) and flows out of the waste liquid hole 321k via the space 321d and the space 321a, or overflows the barrier 321n and flows out of the waste liquid hole 321m via the space 321e and the space 321c, and is then collected in the waste liquid tank 32 in each case. If the detergent is continuously supplied so that the detergent forming the detergent heap sequentially flows out of the space 321b, the sample mixed into the detergent from the sample probe 16 is quickly discharged from the space 321b, thereby preventing the sample from diffusing in the detergent pool. However, the supply of the detergent may be stopped to prevent the detergent from flowing out of the space 321b.

In step Sb5, the mechanism controller 42 causes the sample probe 16 to suck the detergent. More specifically, the mechanism controller 42 causes the dispensing pump 41b to perform the suction operation in a given period to cause the sample probe 16 to suck a certain amount of detergent. Here, the amount of detergent sucked by the sample probe 16 may be changed in accordance with the kind and amount of remaining sample. Moreover, in order to prevent the mixing of the detergent sucked here and the inner water, it is preferable to suck air in accordance with given timing before the suction of the detergent to form an air gap between the inner water and the detergent after the discharge of the remaining sample and the inner water.

The sample probe 16 sucks the detergent as described above, so that the inner wall of the sample probe 16 is washed with the detergent. At the same time, the outer wall of the sample probe 16 contacts the detergent during the above-mentioned suction of the detergent, and the outer wall of the sample probe 16 is thereby washed with the detergent. When the suction of the detergent by the sample probe 16 is finished, the mechanism controller 42 adjusts the supply amount of the detergent pump 41*d* to eliminate the detergent heap.

Figure 17:
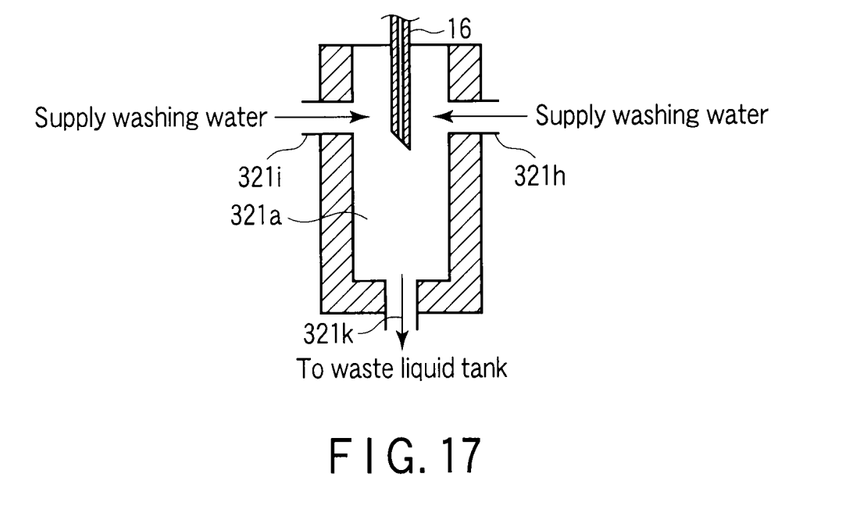
FIG. 17 is a diagram showing the step of washing the sample probe with washing water.

After the suction of the detergent by the sample probe 16 is finished, the mechanism controller 42 moves the sample probe 16 to the first washing position in step Sb6.

In step Sb7, the mechanism controller 42 starts the washing of the outer wall of the sample probe 16 with the washing water and the discharge of the detergent and the inner water. More specifically, the mechanism controller 42 starts the operation of the washing water pump 41*e*, and thereby supplies the washing water retained in the washing water tank 34 to the space 321*a*, providing a washing container, via the water supply holes 321*h* and 321*i*. Thus, as shown in FIG. 17, the outer wall of the sample probe 16 is washed with the washing water blowing from the water supply holes 321*h* and 321*i*. The washing water is collected into the waste liquid tank 32 via the waste liquid hole 321*k*. The mechanism controller 42 also discharges the inner water retained in the inner water tank 22 from the inner water pump 41*c*, and thereby discharges the detergent from the sample probe 16. The mechanism controller 42 then actuates the inner water pump 41*c* until the discharge of the remaining sample is finished and the inner water is discharged from the sample probe 16. The amount of the sucked detergent is known. Therefore, the time for continuing the operation of the inner water pump 41*c* here can be determined in advance in consideration of the amount of the detergent and the discharge volume of the inner water pump 41*c*.

In this way, the inner wall of the sample probe 16 is washed with the inner water after the detergent is discharged.

The detergent and the inner water discharged from the sample probe 16 flow out of the waste liquid hole 321*k* and are collected in the waste liquid tank 32. In this case, if the waste liquid hole 321*k* is aligned along the vertical direction with the intersection of the movement track L1 and the line that connects the water supply hole 321*h* and the water supply hole 321*i*, the waste liquid hole 321*k* is located on the track of the detergent discharged exactly downward from the sample probe 16, so that most of the detergent can be directly passed through the waste liquid hole 321*k*. As a result, the scattering of the detergent in the bottom surface of the space 321*a* can be reduced.

After the outer wall of the sample probe 16 is washed with the washing water for a predetermined period, the mechanism controller 42, in step Sb8, stops the operation of the washing water pump 41*e*, and thus stops the washing of the outer wall of the sample probe 16.

Figure 18:
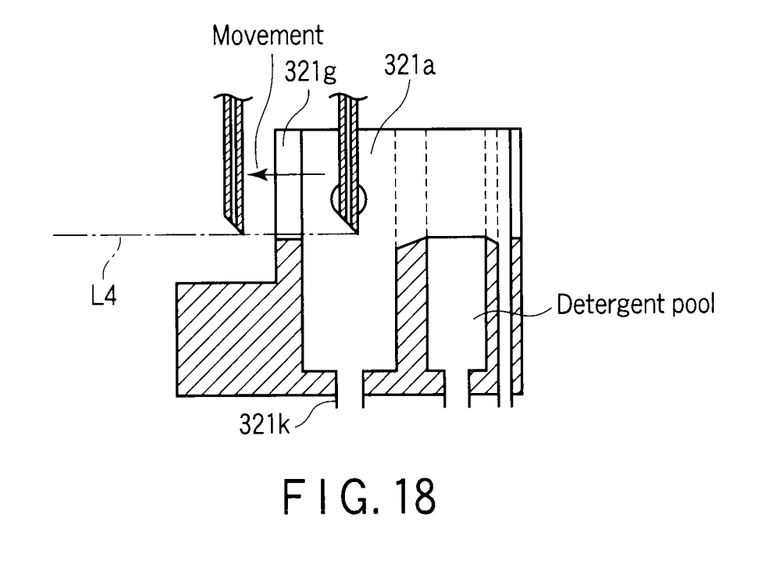
FIG. 18 is a diagram showing the step of moving the sample probe to the outside of the washing basin from the first washing position.

In step Sb9, the mechanism controller 42 moves the sample probe 16 from the first washing position to the outside of the washing basin 31 as shown in FIG. 18. More specifically, the mechanism controller 42 rotates the sample arm 10 to move the sample probe 16 to the outside of the washing basin 31 through the slit 321*g*. A chain line L4 in FIG. 18 indicates the movement track of the distal end of the sample probe 16 in this case.

Thus, the second embodiment allows the discharge of the remaining sample, the washing of the inner wall with the detergent, the washing of the inner wall with the washing water, the washing of the outer wall with the detergent, and the washing of the outer wall with the washing water, without vertical movement of the sample probe 16. Therefore, the sample probe 16 can be efficiently washed in a short time. Alternatively, a long time can be taken for keeping the detergent in the internal flow path 16*b* of the sample probe 16 within a limited time that can be used for one washing of the sample probe 16. This can further ensure the washing of the inner wall.

Furthermore, according to the second embodiment, the space 321*a* for washing the outer wall and the inner wall with the washing water and the space 321*b* in which the detergent pool is formed are separately formed side by side in the horizontal direction, so that the remaining sample and the tainted washing water and detergent do not mixed in the detergent pool. As a result, the efficiency of washing can be improved.

The following various modifications can be made to this embodiment.

The washing unit 30 according to the first and second embodiments may be provided to wash the first reagent probe 14 or the second reagent probe 15. Alternatively, the washing units 30 may be respectively provided to wash any two or all of the first reagent probe 14, the second reagent probe 15, and the sample probe 16. If an additional probe is provided to suck and discharge some liquid matter, a washing unit 30 may be provided to wash this probe.

The time interval and order of the steps shown in FIG. 5 or FIG. 12 may be partly modified. For example, step Sa9 may be performed substantially simultaneously with step Sa8, or may be performed after a predetermined waiting time since step Sa8 has been performed. Moreover, the above-mentioned waiting time may be changed in accordance with the kind of remaining sample. Otherwise, step Sa9 may be started before step Sa8, or step Sa10 may be performed before the completion of step Sa9.

In the first embodiment, the upper space and the lower space may be inverted.

In the first embodiment, the respective washings may be performed in the same space without separately providing the upper space and the lower space.

In the first embodiment, the washing water and the detergent may be supplied from the same supply hole.

In the second embodiment, a flow path switch (not shown) comprising, for example, a change-over valve may be connected via, for example, a tube, and the flow path switch may be further connected to the detergent pump 41*d* and the waste liquid tank 32 via, for example, a tube. After the detergent is sucked by the sample probe 16, the detergent in the space 321*b* may be once collected in the waste liquid tank 32, and a new detergent may then be supplied to the space 321*b* from the detergent tank 33 to form a detergent pool and a detergent heap. In this case, the space 321*c* may be omitted. Moreover, the detergent may be prevented from flowing from the space 321*b* to the space 321*a*.

For example, a space similar to the space 321*c* may be additionally provided between the space 321*a* and the space 321*b*, and the detergent may be discharged to the outside of the washing basin 31 via the additional space. This can prevent the detergent from flowing into the space 321*a*.

Both the first and second embodiments can be intended to wash a nozzle, such as a reagent probe, for sucking and discharging a liquid matter different from a sample.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An automatic analysis apparatus comprising:
    an analyzing unit including a nozzle which comprises a flow path for a sample to be analyzed, and an orifice that opens the flow path to the outside;
    a dispensing pump operatively connected to the nozzle and configured to discharge a fluid in the flow path from the orifice and configured to suck a fluid into the flow path from the orifice;
    a washing basin having a lower wall and a sidewall and forming a lower space located above the lower wall and an upper space located above the lower space along a vertical axis, wherein in the lower wall, a waste liquid hole is formed, and in the sidewall a detergent supply hole connected to the lower space and a water supply hole connected to the upper space are formed, respectively, and wherein in the sidewall of the washing basin an upper waste liquid hole that connects the lower space with the outside of the washing basin is formed at a position lower than the detergent supply hole along the vertical axis;
    a water supplying unit configured to supply washing water into the upper space from the water supply hole;
    a detergent tank and a detergent pump configured to supply detergent into the lower space from the detergent supply hole;
    a vertical movement unit configured to move the nozzle to change the vertical position of the nozzle between a first position where the orifice is located in the upper space container and a second position where the orifice is located in the lower space, wherein each position of the orifice when the nozzle is located in the first and second position, and the waste liquid hole, align along a vertical direction; and
    a control unit configured to sequentially operate the vertical movement unit to locate the nozzle at the second position, operate the fluid discharge device to discharge a fluid in the flow path while the nozzle is located in the second position, operate the detergent tank and the detergent pump to form a detergent pool in the lower space, wherein the detergent pool is maintained at a constant level such that the portion of the detergent pool level with the upper waste hole flows out of the upper waste hole, operate the fluid suction device to suck the detergent into the flow path while the orifice is located in the detergent pool, operate the fluid discharge device to discharge a fluid including the detergent in the flow path while the nozzle is located in the first position, wherein the control unit further operates the supplying unit to supply washing water to blow the washing water to an outer wall of the nozzle from the water supply hole while the nozzle is located in the first position.

2. The automatic analysis apparatus according to claim 1, wherein the detergent tank and the detergent pump supplies the detergent into the lower space at a velocity equal to or more than a velocity at which the detergent is discharged from the waste liquid hole.

3. The automatic analysis apparatus according to claim 1, further comprising:
    a protrusion which is located between the lower space and the upper space without preventing the movement of the nozzle in the washing basin by the vertical movement unit.

4. The automatic analysis apparatus according to claim 1, wherein the control unit changes at least one of the amount of the detergent sucked into the flow path, the kind of the detergent sucked into the flow path, and the time from the end of operating the dispensing pump to suck detergent from the detergent pool into the flow path and the beginning of operating the dispensing pump to discharge the fluid including the detergent in the flow path.

5. The automatic analysis apparatus according to claim 4, wherein the control unit increases the amount of detergent to be sucked into the flow path in accordance with an increase in the viscosity or the quantity of the fluid in the flow path.

6. The automatic analysis apparatus according to claim 4, wherein the control unit increases an alkalinity level of the detergent to be sucked into the flow path in accordance with an increase in the viscosity or the quantity of the fluid in the flow path.

\* \* \* \* \*